United States Patent [19]
Zhang et al.

[11] Patent Number: 6,121,513
[45] Date of Patent: Sep. 19, 2000

[54] SULFONAMIDE RESISTANCE IN PLANTS

[75] Inventors: James Zhang, Palo Alto; Michael Fromm, Kensington, both of Calif.

[73] Assignee: Mendel Biotechnology, Inc., Hayward, Calif.

[21] Appl. No.: 09/347,975

[22] Filed: Jul. 6, 1999

Related U.S. Application Data

[60] Provisional application No. 60/093,478, Jul. 20, 1998.

[51] Int. Cl.[7] .......................... C12N 15/62; C12N 15/29; C12N 15/31; C12N 15/82; A01H 5/00

[52] U.S. Cl. .................. 800/300; 435/69.1; 435/69.7; 435/69.8; 435/69.9; 435/320.1; 435/468; 536/23.2; 536/23.4; 536/23.6; 536/23.7; 536/24.1; 800/278; 800/288; 800/298; 800/260

[58] Field of Search ..................... 800/300, 260, 800/288, 278, 298; 435/320.1, 69.1, 69.7, 69.8, 69.9, 468; 536/23.4, 23.7, 23.2, 24.1, 23.6

[56] References Cited

U.S. PATENT DOCUMENTS

| | | | |
|---|---|---|---|
| 4,757,011 | 7/1988 | Chaleff et al. ................... | 435/172.1 |
| 5,597,717 | 1/1997 | Guerineau ........................ | 800/205 |
| 5,633,444 | 5/1997 | Guerineau et al. ................ | 800/205 |
| 5,719,046 | 2/1998 | Guerineau ........................ | 800/205 |

OTHER PUBLICATIONS

Haung et al. The Plant Cell, vol. 2, pp. 1249–1260, Dec. 1990.

Chaumont et al. Plant Molecular Biology 24: 631–641, 1994.

Boutry et al. Nature vol. 328 pp. 340–342, Jul. 1987.

*Primary Examiner*—David T. Fox
*Assistant Examiner*—Medina A. Ibrahim
*Attorney, Agent, or Firm*—Karen Guerrero

[57] ABSTRACT

Recombinant proteins comprising on or more mitochondrial leader peptide sequences and a domain having herbicidal sulfonamide-insensitive dihydropteroate synthase activity are disclosed. Transformation of plants with nucleic acids that encode this mitochondrially-targeted recombinant protein is also provided. Such transformed plants exhibit resistance to herbicidal sulfonamides, such as asulam, and therefore may be cultivated where such herbicides are being used to control weed growth.

13 Claims, No Drawings

SULFONAMIDE RESISTANCE IN PLANTS

This application claims priority from provisional application Ser. No. 60/093,478, filed Jul. 20, 1998.

FIELD OF THE INVENTION

This invention relates to herbicide resistant plants, and more specifically to plants that are engineered to be resistant to herbicidal sulfonamides. In particular, this invention relates to a transgenic plant expressing a recombinant protein comprising a mitochondrial leader peptide and a functional domain having sulfonamide resistance activity.

BACKGROUND OF THE INVENTION

Weed control is a significant problem for farmers, and the use of herbicides to control weeds and other unwanted plants in cultivated fields has become a nearly universal practice. Broad-spectrum herbicides are particularly useful in combating wide varieties of weeds, but it is not always possible to identify a broad-spectrum herbicide that kills weeds without harming the crop plant. Production of hybrids or engineered crop varieties with specific herbicide resistance provides an attractive solution by allowing an herbicide to be used to kill weeds without significant damage to the resistant crop.

One class of broad-spectrum herbicides that is widely used and has proven particularly efficacious is the herbicidal sulfonamides. These compounds are well known in the art, and their general characteristics are discussed in U.S. Pat. No. 5,719,046. Herbicidal sulfonamides are effective at controlling both monocotyledonous and dicotyledenous weeds, while exhibiting low toxicity to mammals, birds, fish and other wild life. Sulfonamides also have short soil persistence, thereby reducing problems of toxic soil accumulation and run-off contamination.

Sulfonamides act as inhibitors of dihydropteroate synthase (DHPS), an enzyme of the folic acid synthesis pathway. The folic acid synthesis pathway is essential for the production of folic acid cofactors, which are required for the synthesis of purines, thymidylate, glycine, methionine, and several other compounds in all cells. Mammals have a carrier-mediated active transport system that allows mammalian cells to use pre-formed folic acid. In contrast, most microbes and plants lack this active transport system and therefore must synthesize folic acid de novo; they are therefore sensitive to sulfonamides.

Because sulfonamides act as competitive substrates of DHPS, mutations in the gene encoding this enzyme can occur that confer sulfonamide-insensitive DHPS activity. In bacteria, such naturally occurring resistance to sulfonamides is conferred by various bacterial R plasmids. The resistance genes (sul genes) found on R plasmids encode mutant versions of DHPS that are resistant to inhibition by sulfonamides (Guerineau, et al. (1990) Plasmid 23:35–41).

Naturally occurring resistance to herbicides in plants has not been extensively studied. However, two methods have been used to engineer such resistance: random mutagenesis and subsequent selection of resistant varieties; and specific genetic engineering and expression of resistant or insensitive proteins. Some researchers have selected for randomly occurring herbicide resistance through exposure of tissue culture cells to high herbicide levels. See, for instance, U.S. Pat. No. 5,718,079 (providing a method for growing maize with altered, herbicide resistant acetohydroxyacid synthase); and U.S. Pat. No. 4,757,011 (providing tobacco varieties resistant to herbicidal sulfonamides, where the resistance is induced through exposure of tissue cell cultures to inhibitory levels of sulfonamides). Others have mutagenized seed and subsequently selected for herbicide resistance (U.S. Pat. No. 5,084,082, providing soybean plants bearing at least one dominant random heritable mutation capable of conferring resistance to one or more herbicide).

The second method used to engineer resistance to herbicides involves transforming plants with specific nucleotide sequences encoding proteins that have herbicide resistant or insensitive enzyme activity. See, for instance, U.S. Pat. No. 5,605,011 (transformation of plants with sulfonylurea herbicide-insensitive acetolactate synthase, where the modified acetolactate synthase gene was isolated after exposure of cultured plant cells to high levels of a sulfonylurea herbicide).

Previous reports have shown that the sulI gene from bacterial R plasmid R46, when targeted into chloroplasts, confers sulfonamide resistance in plants (See U.S. Pat. Nos. 5,597,717 and 5,633,444). The present invention provides a method for targeting sulfonamide resistance genes to the mitochondrion and may provide optimal resistance.

SUMMARY OF THE INVENTION

We have discovered that sulfonamide resistance in plants may be obtained by expressing a protein having herbicidal sulfonamide-insensitive dihydropteroate synthase (DHPS) activity in plant mitochondria. Proteins having DHPS activity (generically referred to as sul proteins) are known, and include the bacterial proteins sulI and sulII.

One aspect of the invention is thus a recombinant protein comprising first and second domains, wherein the first domain comprises one or more mitochondrial leader peptides, and the second domain has herbicidal sulfonamide-insensitive DHPS activity. The invention also provides recombinant nucleic acid molecules that encode such a recombinant protein, as well as herbicidal sulfonamide-resistant transgenic plants that express the recombinant protein. The expression of sulfonamide resistance in crop plants facilitates the use of herbicidal sulfonamides for weed control in these crops. The expression of sulfonamide resistance in plants and plant cells may be also used as a selectable marker.

In particular embodiments of the invention, the second domain of the recombinant protein is a sul protein and the mitochondrial leader peptide is selected from the group consisting of the mitochondrial leader peptides from: *N. plumbaginifolia* ATPase-beta subunit; yeast cytochrome oxidase subunit Va; mitochondria-specific NADP-isocitrate dehydrogenase (ICDH); NADH-binding subunit of respiratory chain complex I; and yeast mitochondrial tryptophanyl-tRNA-synthetase, for example the fusion protein shown in SEQ ID NO: 1.

The invention also provides nucleic acid molecules encoding the recombinant proteins described above. In one embodiment, such nucleic acid molecules comprise a plant promoter operably linked to an open reading frame that encodes a recombinant protein comprising a mitochondrial leader peptide functionally linked to a domain having herbicidal sulfonamide-insensitive DHPS activity, for example the nucleic acid sequence shown in SEQ ID NO: 2. Nucleic acid vectors and plant cells including these nucleic acid molecules are other aspects of the invention.

In a further aspect, the invention provides a transgenic plant or its progeny comprising a nucleic acid molecule encoding a recombinant protein having first and second domains, wherein the first domain comprises one ore more mitochondrial leader peptides, and the second domain has herbicidal sulfonamide-insensitive DHPS activity. Depending on the mitochondrial leader peptide selected, the leader peptide domain of the recombinant protein may be cleaved off when the protein enters a mitochondrion, leaving the active sulfonamide-insensitive DHPS to function in the organelle. For optimal resistance to herbicidal sulfonamides, at least 25% of the herbicidal sulfonamide-insensitive dihydropteroate synthase recombinant protein is localized in the mitochondria of the plant and a minimal amount, such as none, of the recombinant protein is localized in chloroplasts. More preferably, at least 50%, and more preferably still at least 75% of this protein is localized in the plant mitochondria. The invention also encompasses a method of making an herbicidal sulfonamide-resistant transgenic plant, comprising transforming a plant cell with a nucleic acid molecule and selecting a transformed plant that is resistant to a herbicidal sulfonamide. Plants produced by such a method are also provided by the invention. These and other aspects of the invention are described in more detail in the following sections.

Sequence Listing

SEQ ID NO: 1 shows the amino acid sequence of a *N. plumbaginifolia* ATPase-beta-sulII fusion.

SEQ ID NO: 2 shows a DNA sequence encoding the A TPase-beta-sulII fusion.

SEQ. ID NOs: 3 through 8 show the oligonucleotides used to construct the *N. plumbaginifolia* ATPase-beta mitochondrial leader sequence.

DETAILED DESCRIPTION OF THE INVENTION

Definitions

Unless otherwise noted, technical terms are used according to conventional usage. Definitions of common terms in molecular biology may be found in Benjamin Lewin, *Genes V,* published by Oxford University Press, 1994 (ISBN 0-19-854287-9); Kendrew et al. (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8).

In order to facilitate review of the various embodiments of the invention, the following definitions of terms are provided:

Herbicidal sulfonamide-insensitive dihydropteroate synthase (DHPS) activity: An enzyme displaying biologically significant DHPS activity in the presence of an agriculturally relevant level of an herbicidal sulfonamide is said to have herbicidal sulfonamide-insensitive dihydropteroate synthase activity. Biologically significant DHPS activity is further defined as that level of enzyme activity sufficient to permit a plant or bacterial cell to manufacture essential amounts of dihydropteroate. There is no requirement for the herbicidal sulfonamide-insensitive enzyme, whether engineered or naturally occurring, to display dihydropteroate synthesis activity equal to that of the wild type enzyme from the same species. Herbicidal sulfonamide-insensitive DHPS activity is easily measured qualitatively. Any enzyme that exhibits sufficient DHPS activity to render an otherwise herbicidal sulfonamide-sensitive cell resistant to such a herbicide when the enzyme is expressed will be considered to display herbicidal sulfonamide-insensitive dihydropteroate synthase activity.

Sulfonamides: Anti-bacterial and herbicidal compounds that act as inhibitors of dihydropteroate synthase (DHPS). These compounds generally are analogs of para-aminobenzoic acid (p-ABA) that are recognized by DHPS as alternate substrates (Hong et al. (1995) J. Antimicrob. Chemother. 39:1756–1763) and thereby act as competitive substrates of the enzyme. The term sulfonamide is herein understood to include sulfonamide compounds and the agriculturally acceptable salts thereof.

Herbicidal sulfonamides: Those sulfonamide compounds that are or may be used commercially to control the growth of weeds. Such sulfonamide compounds are well known in the art and are described in many scientific and patent publications, including: U.S. Pat. No. 4,761,373 (Herbicide resistant plants), U.S. Pat. No. 4,724,039 (Herbicidal sulfonamides), U.S. Pat. No. 4,435,206 (Agricultural pyridinesulfonamide), and U.S. Pat. No. 4,370,479 (Herbicidal sulfonamides). Herbicidal sulfonamides of particular interest is methyl sulfanilylcarbamate (also known as asulam or Asulox®).

The herbicides listed herein, structurally related herbicidal compounds, and agriculturally acceptable salts of these compounds, are referred to herein as "herbicidal sulfonamides." Agriculturally acceptable salts are well known in the art, and are disclosed for example in U.S. Pat. No. 5,719,046 (Sulfonamide resistance genes and their use) and U.S. Pat No. 5,498,773 (Herbicide compositions with increased crop safety).

Sensitive to inhibition by an herbicidal sulfonamide: A plant cell, plant or plant species that is unable to grow in the presence of an agriculturally relevant level of an herbicidal sulfonamide is considered sensitive to inhibition by said herbicidal sulfonamide. The use of sulfonamides as herbicides is well known in the art and is generally described, for example, in U.S. Pat. No. 5,719,046 (Sulfonamide resistance genes and their use). By way of example, an agriculturally relevant amount of herbicidal sulfonamide may be from 1.0 to 4.0 asulam equivalents/hectare. The term "asulam equivalents" refers to the amount of another herbicidal sulfonamide necessary to achieve the same level of weed control as that provided by asulam.

Resistance to an herbicidal sulfonamide: The ability of a plant cell, plant or plant species to survive exposure to levels of herbicidal sulfonamide otherwise adequate to inhibit the growth of non-modified specimens of the same species. For the purposes of this specification, such resistance is conferred by the expression of a protein having herbicidal sulfonamide-insensitive DHPS activity. The gene encoding such a protein is referred to as an herbicidal sulfonamide resistance gene, and may be for instance a naturally occurring allele of DHPS (Swedberg, G. (1987) Antimicrob Agents Chemother 31:306–311) or a chemically induced variant of a bacterial or plant gene (U.S. Pat. No. 4,757,011 (Herbicide resistant tobacco)).

Modified dihydropteroate synthase: A protein that is derived from DHPS, either naturally or engineered in the laboratory, that exhibits herbicidal sulfonamide-insensitive DHPS activity when it is expressed in a cell or plant that is otherwise sensitive to inhibition by said herbicidal sulfonamide.

Mitochondrial leader peptide: Most nuclear-encoded mitochondrial proteins are imported into mitochondria due to the presence of a targeting peptide, the mitochondrial leader peptide (Neupert (1997) Ann. Rev. Biochem., 66:863–917). Typically, leader peptides are proteolyzed after the attached protein has been imported into a mitochondrion. Mitochondrial leader peptides can be joined to non-mitochondrial proteins to target the resultant recombinant passenger protein into the mitochondria. A nucleic acid sequence encoding a mitochondrial leader peptide may be obtained through genetic engineering from an existing mitochondrially-targeted protein, for instance *N. plumbaginifolia* ATPase-beta. Alternatively, the coding sequence for a mitochondrial leader peptide may be engineered in the laboratory, for instance through oligonucleotide synthesis. Additionally, it has been demonstrated that tandem duplication of mitochondrial leader peptides can enhance the targeting of some proteins to mitochondria (Galanis et al (1991) FEBS Lett. 282:425–430). It therefore may be useful in some embodiments of this invention to use multiple, tandem copies of a chosen mitochondrial leader sequence in making the transformation construct.

For the purpose of the current invention, mitochondrial leader peptides are quantitatively characterized by the ability to target at least 25% of the stable recombinant protein into the mitochondria. Such mitochondrial leader peptides will more preferably target at least 50% and still more preferably at least 75% of the stable recombinant protein into the mitochondria. The amount of mitochondrially-targeted recombinant protein can be measured by cellular fractionation followed by quantitative immunoblot analysis using a antiserum specific to the recombinant protein. A percentage measurement of the DHPS protein targeted to the mitochondria may be calculated by comparing the densitometric signal given by the protein in equivalent (measured by number of cells or grams of plant tissue) amounts of total cell, mitochondrial, and cytosolic fractions.

Alternatively, if desired, the activity of the recombinant targeted protein may be measured using a standard quantitative activity assay after fractionation of the cell. For instance, cell fractions may be assayed for DHPS activity as described by Neuburger et al. (1996) J. Biol. Chem. 271:9466–9472. A percentage measurement of the DHPS activity targeted to the mitochondria may be calculated by comparing the assayed activity level of equivalent (measured by number of cells or grams of plant tissue) amounts of total cell, mitochondrial, and cytosolic fractions. A mitochondrial leader peptide will typically target at least 30% of the transgene-encoded herbicidal sulfonamide-insensitive DHPS activity to the mitochondria. Higher percentages of mitochondrially-targeted activity of herbicidal sulfonamide-insensitive DHPS activity (e.g. at least 50%, 60%, or 70%) may be obtained using particular leader peptide sequences, and may correlate with resistance to higher levels of herbicidal sulfonamide.

A sul gene: Any gene encoding a protein having herbicidal sulfonamide-insensitive DHPS activity. Bacterial resistance genes encode mutant versions of DHPS that are resistant to inhibition by sulfonamides. Such bacterial genes include specifically the R plasmid R46 DHPS gene sulI (Guerineau and Mullineaux (1989) Nucleic Acids Res. 17:4370) and the R plasmid RSF1010 DHPS gene sulII (R ȧdström and Swedberg (1988) Antimicrob. Agents Chemother. 32:1684–1692).

A sul protein: The protein product of a sul gene.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Transgenic plant: As used herein, this term refers to a plant or plant material (seeds, plant cells, and the like) that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

The present invention entails use of a DHPS-activity conferring enzyme fused to a heterologous mitochondrial leader sequence. Since the plant enzyme harboring DHPS activity is homologous to bacterial DHPS (Rebeille, F., et al. (1997) EMBO J. 16(5):947–957), plant genes encoding proteins having sulfonamide-insensitive DHPS activity may be isolated based on their sequence homology to bacterial DHPS. In bacteria, sulfonamide-insensitive enzymes having DHPS activity are carried on various R plasmids (Ṙadström and Swedberg supra; Guerineau et al., Guerineau, et al. (1990) Plasmid 23(1):35–41) and on transposons such as Tn21 (Sundström (1988) Mol Gen Genet 213:191–201).

Both conventional hybridization and PCR amplification procedures can be utilized to isolate and clone such sequences. Common to both of these techniques is the hybridization of probes or primers derived from the bacterial DHPS gene sequence, or homologs of this sequence, to a target nucleotide preparation. This target nucleotide preparation may be, in the case of conventional hybridization approaches, a cDNA or genomic library or, in the case of PCR amplification, a cDNA or genomic library, or an mRNA preparation. By way of example, such probes or primers may be selected based on the nucleotide sequence of the sulI (Sundström et al, supra) or sulII (Ṙadström and Swedberg, supra) genes.

Direct PCR amplification can be performed on cDNA or genomic libraries prepared from the plant species in question, or RT-PCR can be performed using mRNA extracted from the plant cells using standard methods. PCR primers can comprise at least 15 consecutive nucleotides of the bacterial DHPS gene. One of skill in the art will appreciate that sequence differences between the bacterial DHPS gene and the target nucleic acid to be amplified may result in lower amplification efficiencies. Longer PCR primers or lower annealing temperatures may be used during the amplification cycle to compensate for this. Where lower annealing temperatures are used, sequential rounds of amplification using nested primer pairs can be necessary to enhance specificity.

For conventional hybridization techniques the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the bacterial gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

The selection of PCR primers will be made according to the portions of the gene that are to be amplified. Primers may be chosen to amplify small segments of the gene, the open reading frame or the entire gene sequence. Variations in amplification conditions may be required to accommodate primers of differing lengths; such considerations are well known in the art and are discussed in Innis et al. (1990) *PCR Protocols, A Guide to Methods and Applications*, Academic Press, Inc., San Diego, Calif.). It will be appreciated by one skilled in the art that many different primers may be derived from the published gene sequences for DHPS in order to amplify particular regions of these molecules. In addition, it is well known in the art to engineer specific restriction endonuclease cleavage sites into such primers in order to facilitate subsequent cloning of the amplified sequence. Resequencing of PCR products obtained by amplification procedures is recommended; this will facilitate confirmation of the amplified sequence as well as any engineered restriction endonuclease cleavage sites, and will provide information on natural variation of the protein sequence in different ecotypes and plant populations.

Where a transformed gene will be integrated into the nuclear genome of the plant cell, and it is necessary to target the expressed protein into a specific subcellular organelle or to the extracellular matrix to ensure its proper function in vivo, a targeting sequence specific to that subcellular location should be included in the plant transformation construct. Proteins that are expressed in the plant mitochondria are generally targeted to this location by an amino terminal-extension called the mitochondrial leader peptide. Several plant mitochondrial proteins have been studied and their leader peptides are known to those skilled in the art, for example superoxide dismutase, cytochrome c1, mitochondrial F1-ATPase beta-subunit, and the NADH-binding subunit of respiratory chain complex I. Certain plant leader peptides have been studied in in vitro import systems for their protein import characteristics, for example *N. plumbaginifolia* and *Neurospora crassa* F1-ATPase-beta import into isolated spinach leaf mitochondria.

In addition, some plant leader peptides have been used to target recombinant heterologous passenger proteins into the mitochondria of transgenic plants. See, Boutry et al (1987) Nature 328:340–342 (using a 90 amino acid segment of the amino terminus of *N. plumbaginifolia* ATPase-beta to target CAT). Certain non-plant mitochondrial leader peptides have also been used to target recombinant heterologous passenger proteins into plant mitochondria (Huang et al. (1990) Plant Cell 2:1249–1260 (using yeast mitochondrial cytochrome oxidase subunit Va leader to target CAT into transgenic tobacco organelles)). A person of ordinary skill in the art will be able to choose one or more appropriate mitochondrial leader peptides for use in the current invention. The experiments discussed here are given by way of example only, and are not intended to limit those mitochondrial leader peptides that may be used in the current invention.

It has been demonstrated that tandem duplication of mitochondrial leader peptides can enhance the targeting of some proteins to mitochondria (Galanis et al. (1991) FEBS Lett. 282:425–430). It therefore may be useful in some embodiments of this invention to use multiple, tandem copies of a chosen mitochondrial leader sequence in making the transformation construct. This will be especially useful where the amount of protein targeted to the mitochondria is low with only a single such leader.

By way of example only, the mitochondrial leader peptides of yeast cytochrome oxidase subunit Va, *N. plumbaginifolia* F1-ATPase-beta subunit, mitochondria-specific NADP-ICDH (Galvez et al. (1998) Proc. Natl. Acad. Sci. USA 95:7813–7818), NADH-binding subunit of respiratory chain complex I (Grohmann et al. (1996) Plant J. 10:793–803), and yeast mitochondrial tryptophanyl-tRNA-synthetase (Schmitz and Lonsdale (1989) Plant Cell 1:783–791) can be used in the invention.

Once a nucleic acid encoding a recombinant protein has been produced, standard techniques may be used to express the nucleic acid in transgenic plants. The basic approach is to clone the nucleic acid into a transformation vector, such that it is operably linked to control sequences (e.g., a promoter) that direct expression of the nucleic acid in plant cells. The transformation vector is then introduced into plant cells by one of a number of techniques (e.g., electroporation) and progeny plants containing the introduced nucleic acid are selected. Preferably all or part of the transformation vector will stably integrate into the genome of the plant cell. The part of the transformation vector that integrates into the plant cell, and which contains the introduced nucleic acid and associated sequences for controlling expression (the introduced "transgene"), may be referred to as the recombinant expression cassette. Selection of progeny plants containing the introduced transgene may be made based upon the detection of an altered phenotype, such as sulfonamide resistance.

Successful examples of the modification of plant characteristics by transformation with cloned gene or cDNA sequences are replete in the technical and scientific literature. Selected examples, which serve to illustrate the current knowledge in this field of technology, and which are herein incorporated by reference, include: U.S. Pat. Nos. 5,597,717; 5,633,444; and 5,719,046 to Guerineau (modification of plant herbicide resistance through expression of sulfonamide-resistant bacterial dihydropteroate synthase directed to the chloroplast); U.S. Pat. No. 5,605,011 to Bedbrook (modification of plant herbicide resistance through expression of sulfonylurea-resistant acetolactate synthase);

These patents include descriptions of transformation vector selection, transformation techniques and the assembly of constructs designed to over-express the introduced nucleic acid. In light of the foregoing, and the provision herein of a construct comprising a mitochondrial leader sequence fused to a gene encoding a protein that displays herbicidal sulfonamide-insensitive DHPS activity, it is apparent that one of skill in the art will be able to introduce these nucleic acid molecules, or homologous or derivative forms of these molecules, into plants in order to produce plants having herbicidal sulfonamide-insensitive DHPS activity.

The folic acid synthesis pathway is found in all plant types. Recombinant nucleic acid molecules according to the present invention (e.g., an herbicidal sulfonamide-insensitive DHPS activity-conferring nucleic acid molecule and homologs, derivatives and variants of such sequences, operably linked to a mitochondrial leader sequence) may be introduced into any plant type in order to modify DHPS activity in the plant. The constructs of the present invention thus may be used to modify DHPS activity in any higher plant, including both monocotyledonous and dicotyledenous plants. Such plants include, but are not limited to Arabidopsis, maize, wheat, rice, barley, sorghum, soybean, beans in general, rape/canola, alfalfa, flax, sunflower, safflower, brassica, cotton, flax, peanut, clover, sugarbeet, sugarcane, turf and fescue grasses; vegetables such as lettuce, tomato, cucurbits, potato, carrot, radish, pea, lentils, cabbage, broccoli, brussel sprouts, peppers; trees such as apples, pears, peaches, apricots, pine, poplar, and eucalyptus; and flowers such as carnations and roses.

A number of recombinant vectors suitable for stable transformation of plant cells or for the establishment of transgenic plants have been described, including those described in Weissbach & Weissbach (1989) *Methods for Plant Molecular Biology*, Academic Press, Gelvin et al. (1990) *Plant Molecular Biology Manual*, Kluwer Academic Publishers, and Jones et al. (1992) Transgenic Research 1:285–297). Typically, plant transformation vectors include one or more cloned plant genes (or cDNAs) under the transcriptional control of 5' and 3' regulatory sequences, and a dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters which may be useful for expressing the disclosed nucleic acid molecule include: cauliflower mosaic virus (CaMV) 35S promoter, which confers constitutive, high-level expression in most plant tissues (Benfey & Chua (1990) Science 250:959–966; nopaline synthase promoter (An et al. (1988) Plant Physiol. 88:547); and octopine synthase promoter (Fromm et al. (1989) Plant Cell 1:977). Constitutive expression throughout the plant is preferred; however, spatial or temporal regulation of expression of the provided nucleic acid molecule may be accomplished. A variety of plant gene promoters that are regulated in response to environmental, hormonal, chemical, and/or developmental signals can be used for expression of the nucleic acid molecule in plant cells.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato, or the octopine or nopaline synthase 3' terminator regions. Because the nucleic acid molecule provided herein confers herbicidal sulfonamide resistance on transformed cells, it is likely that no other selectable marker gene is required for the selection of transformants. Successful transformants may be selected for by growth on medium containing a sulfonamide, as discussed in more detail below.

Transformation and regeneration of both monocotyledonous and dicotyledenous plant cells is now routine; selection of the most appropriate transformation technique will be determined by the practitioner. The choice of technique will vary with the type of plant to be transformed; those skilled in the art will recognize the suitability of particular methods for given plant types. Suitable methods may include, but are not limited to electroporation of plant protoplasts, liposome-mediated transformation, polyethylene glycol (PEG) mediated transformation, transformation using viruses, micro-injection of plant cells, micro-projectile bombardment of plant cells, vacuum infiltration, and *Agrobacterium tumefaciens* (AT)-mediated transformation. Typical procedures for transforming and regenerating plants are described in the patent documents listed at the beginning of this example.

Following transformation of plants with the transformation vector and, where necessary, regeneration of the plants from tissue culture or cells, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic. For the present invention, the preferred selection is on asulam, sulfadiazine, or another herbicidal sulfonamide.

Sulfonamide resistant seeds can also be selected by attempting germination of transformed seeds on medium containing sulfadiazine. For instance, untransformed wild type seeds are unable to germinate on medium containing 20 μg/ml of sulfadiazine, whereas seeds that have been transformed with the provided sulfonamide-insensitive DHPS will germinate well on medium containing sulfadiazine concentrations of up to 200 μg/ml.

As a third alternative, transformed seeds can be selected for by incubation in asulam prior to germination. Seeds collected from the transformation pots are surface sterilized essentially as described above, then incubated overnight in an aqueous solution of about 0.1% asulam. Untransformed wild type seeds are unable to germinate after such treatment, whereas seeds that have been transformed with the provided sulfonamide-insensitive DHPS will germinate well.

Localization of the sulfonamide-insensitive DHPS protein to the plant mitochondria is preferred. Preferably, at least 25% (and more preferably at least 50% or still more preferably at least 75%) of the herbicidal sulfonamide-insensitive DHPS protein accumulates in the mitochondria of plants transformed with the disclosed nucleic acid. Preferably, none or very little of the DHPS protein accumulates in the chloroplast. The subcellular localization of a specific protein or its activity may be determined by many techniques well known in the art. The first required step is that the plant cell be fractionated at least into a mitochondrial fraction and remaining cellular constituents. Optionally, further fractionation of the non-mitochondrial material into chloroplastic, cytosolic, nuclear, and extracellular fractions can be carried out. Techniques for fractionation of the plant cell are well known in the art, and have been described.

EXAMPLE 1

Selection of a Gene Exhibiting Herbicidal Sulfonamide Insensitive DHPS Activity

By way of example only, the sulII coding sequence from R plasmid RSF1010 (Radström and Swedberg (1988) supra) was amplified using two oligonucleotide primers (A=5' AAGCC CCCATGGATAAATCGCTCATCATTTTC 3' SEQ ID NO: 9 and B=5' GCTCTAGATTAACGAATCCTT GCGGTTTCTTTCAGCG 3' SEQ ID NO: 10). To facilitate subsequent cloning, a NcoI site was engineered at the translation initiation of primer A and the EcoRI site was removed by a silent mutation and an XbaI site added to the beginning of primer B. The primers were used for PCR amplification using R plasmid RSF1010 as the template. A fragment of the expected size (840 bp) was obtained. The sequence of the PCR fragment indicated that the product was the correct sulII gene.

EXAMPLE 2

Selection of a Mitochondrial Leader Peptide and Construction of a Mitochondrial Leader-SulII Fusion Construct The following plasmids can be used in this invention: plasmids SLJ4D4 and SLJ4K1 (Jones et al. (1992) supra). Briefly, pSLJ4D4 contains the 35S promoter, the omega translation enhancer, the uidA gene, and the ocs terminator, while pSLJ4K1 contains the 35S promoter, the omega translation enhancer, the uidA gene, and the nos terminator.

Plasmid MEN002 contains no targeting sequence and was obtained by ligating the NcoI and XbaI digested sulII PCR product into the NcoI and XbaI sites of pSLJ4D4.

Plasmid MEN004 contains the mitochondrial leader peptide of N. plumbaginifolia ATPase-beta (Boutry et al. (1987) supra). The coding sequence of the leader peptide was engineered by annealing 6 oligonucleotides, namely SEQ. ID NOS: 3–8, and ligating them together using T4 DNA ligase. To generate a fusion protein, two extra bases and an NcoI site were added to the 3' end of the coding sequence of the mitochondrial leader peptide and a cohesive ClaI site was added to the 5' end of the coding sequence. It was then ligated with two other fragments, the vector portion of ClaI/XbaI-digested pSLJ4K1, and the PCR fragment of the sulII gene digested with NcoI and XbaI.

Plasmid SLJ7292 is a binary vector that confers tetracyclin resistance in bacteria and kanamycin resistance in plants (Jones et al. (1992) supra). The specific plant transformation vectors pMEN005, and pMEN007 were constructed by cutting out the inserts from pMEN002, and pMEN004 with EcoRI and HindIII, then ligating these fragments into the EcoRI and HindIII sites of pSLJ7292.

EXAMPLE 3

Plant Transformation

Agrobacterium strain GV3101 can be used as described by Bechtold et al. (1993) C.R. Acad. Sci. Paris, Sciences de la vie/Life Sciences 316:1194–1199. Single Agrobacterium colonies containing each of the constructs described above was used to inoculate 500 ml cultures (LB medium containing 5 µg/L tetracyclin and 15 µg/L gentamycin) for plant transformation. Cultures were grown at 28° C. with shaking for 2 days until an absorbance ($A_{600}$) of >2.0 was reached. Cells were then harvested by centrifugation at 4,000×g for 10 minutes, and resuspended in infiltration medium [½×Murashige and Skoog salts (Sigma), 1×Gamborg's B-5 vitamins (Sigma), 5.0% sucrose (Sigma), 0.044 µM benzylamino purine (Sigma), 200 µl/L Silwet L-77 (Lehle Seeds, Round Rock, Tex.)] until an absorbance ($A_{600}$) of 0.8 was reached.

Prior to transformation, Arabidopsis thaliana seeds (ecotype Columbia) were sown at a density of about 10 plants per 4" pot onto Pro-Mix BX potting medium (Hummert International, Earth City, Mo.) covered with fiberglass mesh (18 mm×16 mm). Plants were then grown under continuous illumination (50–75 µE/m²/sec) at 22–23° C. with 65–70% relative humidity. After about 4 weeks, primary inflorescence stems (bolts) were cut off to encourage growth of multiple secondary bolts. After mature secondary bolts were flowering, plants were prepared for transformation by the removal of all siliques and open flowers.

Pots were immersed upside down in the Agrobacterium infiltration medium mixture (described above) for 30 seconds. Pots were then placed on their sides and allowed to drain into a 1'×2' flat covered with plastic wrap. After 24 hours, the plastic wrap was removed and pots turned upright. The immersion procedure was repeated one week later, for a total of two immersions per pot.

EXAMPLE 4

Sulfonamide Resistance of Transformed Plants

Seeds collected from the transformation pots produced as above were surface sterilized essentially as recommended by Lehle Seeds. Seeds were shaken in a solution of 0.1% (v/v) Triton X-100 (Sigma) and sterile $H_2O$ for 20 minutes. Wash solution was then removed and replaced with fresh wash solution. Seeds were again allowed to shake for 20 minutes. After the removal of the second wash solution, a solution of 0.1% (v/v) Triton X-100 and 95% EtOH (Equistar) was added to the seeds. Seeds were allowed to shake in this solution for 5 minutes. After removal of the ethanol/detergent mixture, a solution of 0.1% (v/v) Triton X-100 and 30% (v/v) bleach (Clorox) was added to the seeds. Seeds were then allowed to shake for 10 minutes. After removal of the bleach/detergent mixture, seeds were then washed five times in sterile distilled $H_2O$.

Seeds were stored in the last water wash at 4° C. for 2 days in the dark before being planted in soil (Pro-Mix BX potting medium). Seeds germinated under continuous illumination (50–75 µE/m²/sec) at 22–23° C. At specified time intervals as indicated in Tables 1 for transgenic plants and 2 for wild type plants, plants were sprayed with sulfonamide (Asulox® herbicide, Rhone-Poulenc Agrochemie) at specified concentrations in the presence of Silwet L-77 (200 microliter/ml) (Lehle Seeds). Observations were made 28 days after planting.

TABLE 1

| Age of Plants at Spraying (Days) | 0 | 7 | 14 | 21 | 28 |
|---|---|---|---|---|---|
| No spray | − | − | − | − | − |
| Silwet L-77 | − | − | + | − | − |
| 0.05% w/v Asulox | * | +++ | +++ | + | + |
| 0.1% w/v Asulox | * | +++ | ++ | + | − |
| 0.5% w/v Asulox | * | ++ | +++ | ++ | ++ |
| 1.0% w/v Asulox | * | +++ | +++ | ++ | ++ |
| 2.0% w/v Asulox | * | +++ | +++ | ++ | ++ |

TABLE 2

| Age of Plants at Spraying (Days) | 0 | 7 | 14 | 21 | 28 |
|---|---|---|---|---|---|
| No spray | − | − | − | − | − |
| Silwet L-77 | − | − | − | − | − |
| 0.05% w/v Asulox | * | * | * | * | * |
| 0.1% w/v Asulox | * | * | * | * | * |
| 0.5% w/v Asulox | * | * | * | * | * |
| 1.0% w/v Asulox | * | * | * | * | * |
| 2.0% w/v Asulox | * | * | * | * | * |

Where the symbol "−" indicates that plants show no visible sign of distress, "+" indicates plants show some signs of distress, "+++" indicates that plants were visibly distressed and "*" indicates that the plants died. As shown in Tables 1 and 2, targeting the DHPS activity into the mitochondrion allows growth of the plants at high concentrations of environmental sulfonamides.

EXAMPLE 5

Analysis of Progeny of Transformed Plants

Seeds harvested from two self-fertilized transformed plants and seed from an untransformed wild type plant were germinated on medium containing various conentrations of sulfadiazine. Seedlings from wild type plants died soon after germination on 20 micrograms/ml sulfadiazine, whereas transformed seedlings developed normally on sulfadiazine at concentrations up to 200 micrograms/ml. The growth of transformed seedlings was slightly reduced on 500 micrograms/ml sulfadiazine.

The segregation of sulfonamide resistance was about 3 to 1 which was to be expected from a dominant character encoded by a determinant integrated into the genome at one locus.

EXAMPLE 6

DHPS Localization

Desired cell fractions can be isolated as described by Boutry et al. (1987). Plant tissue is homogenized in a buffered and osmotically balanced solution, for instance 0.33 M sucrose, 50 mM Tris HCl (pH 8.0), 0.2% bovine serum albumin (BSA), 0.1% ascorbic acid, and 0.05% β-mercaptoethanol (βME). The homogenate is then filtered to remove large cellular debris. This crude homogenate can be separated into crude cytosolic (supernatant) and crude organellar (pellet) fractions by centrifugation at full speed in an Eppendorf microfuge for 10 minutes.

To isolate purified organelles from the crude plant homogenate, the crude homogenate is centrifuged at 6,000 rpm for 30 seconds in a Sorvall SS34 rotor to pellet a crude chloroplast fraction. This crude chloroplast fraction is then further purified by centrifugation through a two step Percoll gradient (4 ml 80% Percoll and 5 ml 40% Percoll, both with 0.1% BSA) in a suspension medium, for example, 2 ml of 0.4 M mannitol, 10 mM $K_2HPO_4$ (pH 7.2), with 0.1% BSA. After this gradient is centrifuged for 10 minutes in a Sorvall HB4 rotor, the interface containing purified chloroplasts is recovered. For best recovery of chloroplasts, the starting material should be a photosynthesizing plant tissue, for instance leaves.

Mitochondria can be purified in a similar manner. The supernatant from above the crude chloroplast fraction is further centrifuged at 15,000 rpm for 12 minutes in a Sorvall SS34 rotor to yield a crude mitochondrial pellet fraction. This pellet is resuspended in 2 ml of the same resuspension medium as above, then centrifuged through a two-step Percoll gradient (3 ml 40% Percoll and 4.5 ml 21% Percoll, both with 0.1% BSA) for 30 minutes at 20,000 rpm in a Beckman SW28 rotor. Purified mitochondria are recovered from the interface. Alternately, mitochondria can be purified using a self-generating Percoll gradient.

A cytosol-enriched fraction may be used as a comparision. For instance, the supernatant remaining after mitochondrial purification is substantially enriched for cytosolic proteins. Alternately, plant material can be homogenized in a buffered and osmotically balanced lysis medium, for instance 0.3 M mannitol, 20 mM sodium pyrophosphate (pH 7.5), 0.5% polyvinylpyrrolidone, 10 mM βME, 15 mM malate, 10% glycerol, and 1 mM phenylmethylsulfonyl fluoride. This crude extract is then filtered to remove gross cellular debris, and the filtrate cleared by centrifuged at 1500×g. Organellar material is then removed by centrifugation at 18,000×g, to yield a cytosol-enriched fraction. This fraction optionally may be concentrated using a Diaflow XM-10 membrane and an Amicon stirred cell, for instance.

Once the plant cell is fractionated, it is next necessary to measure the amount of modified DHPS protein found in each relevant fraction, for instance the isolated mitochondria compared to the amount found in whole cells. Measurements of specific proteins may be carried out through many techniques well known to those of ordinary skilled in the art. These include quantitative immunoblot analysis (Kieselbach et al. (1998) J. Biol. Chem. 273:7610–6716), as well as enzyme activity assays (when fractionation has been carried out under conditions that preserve DHPS activity) (Neuburger (1996) supra).

Quantitative immunoblot analysis refers to a method of measuring the actual amount of a stable protein present in a cell or cell fraction. Such analysis is well known in the art. In general, proteins from cell fractions are precipitated using trichloracetic acid, then resuspended in SDS-sample buffer and subjected to polyacrylamide gel electrophoresis (PAGE) to separate individual proteins by size. The resultant gel is then electrophoretically transferred ("western blotted") to a nitrocellulose sheet or other equivalent substrate, and subjected to immunoblot analysis using antibodies (either monoclonal or polyclonal) to the protein(s) of interest. It is advantageous to use polyclonal or more preferably monoclonal antibody to the engineered DHPS protein to probe the western blot. Because bacterial DHPS is a smaller, monofunctional protein (Rebeille et al. (1997) supra) it will have a different molecular weight than the endogenous plant DHPS; this allows differentiation between the two proteins on the immunoblot in the instance that antisera to the engineered DHPS protein also recognizes the endogenous protein. Optionally, though especially if the engineered and endogenous proteins are of similar size, an epitope tag can be added to the engineered protein for differential detection. The use of epitope tags is well known.

Primary antibody binding is detected using a secondary antibody, which itself is chemically linked to an indicator molecule. The indicator molecule can be an enzymatically active protein that catalyzes a reaction, the end product of which produces fluorescence. The relative amount of each protein (e.g. DHPS) in different cell fractions is then calculated based on densitometric measurement of the fluorescence signal recorded on exposed x-ray film. Protein standards of known subcellular localization may be used for comparison. A percentage measurement of the DHPS targeted to the mitochondria may be calculated by comparing the densitometric signal given by the protein in equivalent (measured by number of cells or grams of plant tissue) amounts of total cell, mitochondrial, and cytosolic fractions. Further fractions may be characterized for comparison.

Quantification of the amount of DHPS targeted to the mitochondria in this invention alternatively may be carried out through an activity assay. Plant cell fractions prepared as previously described may be assayed for DHPS activity as described by Neuburger (1996). Adequate fractionated sample to provided 5 to 50 mg ml$^{-1}$ of protein is suspended in 120 μl of reaction buffer (20 mM Tris, 20 mM $K_2HPO_4$ (pH 8.0), 20 mM βME, 15 mM $MgCl_2$). 2 μl of 2 mM p-[carboxyl-$^{14}$C]aminobenzoic acid (1.85 GBq mmol$^{-1}$) is added to the assay medium, and the reaction started by the addition of dihydropterin pyrophosphate to a final concentration of 100 μM. The reaction is stopped after 5 minutes by incubation at 100° C. for 5 minutes. The amount of [$^{14}$C] dihydropteroate formed may be estimated using a reverse-phase HPLC system (Nova-Pak C18 column, Waters) coupled with a Berthold LB 506D scintillation counter. The HPLC conditions are as follows: solvent A, 0.1 M sodium acetate (pH 6.0); and solvent B, acetonitrile. Solvent B is increased linearly 1% every minute. Optionally, organellar fractions can be further disrupted by sonication or through the addition of small quantities of non-ionic detergents prior to DHPS activity assays to ensure access of all the active protein to the substrate. A percentage measurement of the DHPS activity targeted to the mitochondria may be calculated by comparing the assayed activity level of equivalent (measured by number of cells or grams of plant tissue) amounts of total cell, mitochondrial, and cytosolic fractions. Further fractions may be characterized for comparison.

To determine the portion of DHPS activity that is contributed by the herbicidal sulfonamide-insensitive DHPS, the above activity assay is repeated in the presence of a level of herbicidal sulfonamide adequate to inhibit the activity of the endogenous plant enzyme, and the activities compared. By way of example only, 20 μg/ml of sulfadiazine may be used for this purpose; however, one skilled in the art will appreciate that the actual amount will be dependent on the plant type and herbicide used. The actual required level may be easily determined by performing activity assays using wild type plant tissue fractions in increasing amounts of herbicidal sulfonamide.

The foregoing examples are provided by way of illustration only. One of ordinary skill in the art will appreciate that numerous variations on the biological molecules and methods described above may be employed to produce plants having resistance to herbicidal sulfonamides. We claim all such subject matter that falls within the scope and spirit of the following claims.

What is claimed is:

1. A transgenic plant comprising a nucleic acid molecule encoding a recombinant protein having first and second domains, wherein the first domain comprises one or more mitochondrial leader peptides functionally linked to the second domain and the second domain has herbicidal sulfonamide-insensitive dihydropteroate synthase activity from a bacterial sul gene, wherein said recombinant protein is localized in the mitochondria and none is localized in the chloroplasts and said recombinant protein is effective to render the plant resistant to sulfonamide.

2. The transgenic plant according to claim 1 wherein the herbicidal sulfonamide-insensitive dihydropteroate synthase is selected from the group consisting of sulI and sulII.

3. The transgenic plant according to claim 1 wherein the mitochondrial leader peptide is selected from the group consisting of the mitochondrial leader peptides from:
   (a) β-subunit of *Nicotiana plumbaginifolia* mitochondrial ATP synthase;
   (b) mitochondria-specific NADP-dependent isocitrate dehydrogenase;
   (c) NADH-binding subunit of respiratory chain complex I; and
   (d) yeast mitochondrial tryptophanyl-tRNA-synthetase.

4. A method of making an herbicidal sulfonamide-resistant transgenic plant, comprising:
   (i) transforming a plant with a nucleic acid molecule comprising an open reading frame, wherein the open reading frame encodes a recombinant protein comprising one or more mitochondrial leader peptides functionally linked to a domain having herbicidal sulfonamide-insensitive dihydropteroate synthase activity from a bacterial sul gene, wherein said recombinant protein is localized in the mitochondria and none is localized in the chloroplasts and said recombinant protein is effective to render the plant resistant to sulfonamide; and
   (ii) selecting a transformed plant that is resistant to a sulfonamide.

5. An herbicidal sulfonamide-resistant transgenic plant produced by crossing or selfing a plant selected from the group consisting of:
   (a) a plant according to claim 1; and
   (b) progeny of a plant according to claim 1.

6. Seed of a plant according to claim 1.

7. A nucleic acid molecule comprising an open reading frame, wherein the open reading frame encodes a recombinant protein comprising one or more mitochondrial leader peptides functionally linked to a domain having herbicidal sulfonamide-insensitive dihydropteroate synthase activity from a bacterial sul gene, wherein said recombinant protein is localized in the mitochondria and none is localized in the chloroplasts and said recombinant protein is effective to render a transgenic plant comprising the nucleic acid molecule resistant to sulfonamide.

8. The nucleic acid molecule according to claim 7 wherein the domain having herbicidal sulfonamide-insensitive dihydropteroate synthase activity is sulI or sulII.

9. The nucleic acid molecule according to claim 7 wherein the mitochondrial leader peptide is selected from the group consisting of the mitochondrial leader peptides from:
   (a) β-subunit of *Nicotiana plumbaginifolia* mitochondrial ATP synthase;
   (b) mitochondria-specific NADP-dependent isocitrate dehydrogenase;
   (c) NADH-binding subunit of respiratory chain complex I; and
   (d) yeast mitochondrial tryptophanyl-tRNA-synthetase.

10. A nucleic acid vector comprising the nucleic acid molecule according to claim 7.

11. A transgenic plant comprising a nucleic acid molecule encoding a recombinant protein having first and second domains, wherein the first domain comprises one or more mitochondrial leader peptides functionally linked to the second domain and the second domain has herbicidal sulfonamide-insensitive dihydropteroate synthase activity from a bacterial sul gene, wherein said mitochondrial leader peptide is selected from the group consisting of the leader peptides from:

(a) the beta-subunit of *Nicotiana plumbaginifolia* mitochondrial ATP synthase;

(b) mitochondria-specific NADP-dependent isocitrate dehydrogenase;

(c) NADPH-binding subunit of respiratory chain complex I; and (d) yeast mitochondiral tryptophanyl-tRNA-synthetase.

12. A method of making an herbicidal sulfonamide-resistant transgenic plant, comprising:

(i) transforming a plant with a nucleic acid molecule comprising an open reading frame, wherein the open reading frame encodes a recombinant protein comprising one or more mitochondrial leader peptides functionally linked to a domain having herbicidal sulfonamide-insensitive dihydropteroate synthase activity from a bacterial sul gene, wherein said mitochondrial leader peptide is selected from the group consisting of the leader peptides from:

(a) the beta-subunit of *Nicotiana plumbaginifolia* mitochondrial ATP synthase;

(b) mitochondria-specific NADP-dependent isocitrate dehydrogenase;

(c) NADPH-binding subunit of respiratory chain complex I; and (d) yeast mitochondiral tryptophanyl-tRNA-synthetase; and (ii) selecting a transformed plant that is resistant to a sulfonamide.

13. A nucleic acid molecule comprising an open reading frame, wherein the open reading frame encodes a recombinant protein comprising one or more mitochondrial leader peptides functionally linked to a domain having herbicidal sulfonamide-insensitive dihydropteroate synthase activity from a bacterial sul gene, wherein said mitochondrial leader peptide is selected from the group consisting of the leader peptides from:

(a) the beta-subunit of *Nicotiana plumbaginifolia* mitochondrial ATP synthase;

(b) mitochondria-specific NADP-dependent isocitrate dehydrogenase;

(c) NADPH-binding subunit of respiratory chain complex I; and (d) yeast mitochondiral tryptophanyl-tRNA-synthetase.

* * * * *

SEQUENCE LISTING

```
<160> NUMBER OF SEQ ID NOS:  10

<210> SEQ ID NO 1
<211> LENGTH: 362
<212> TYPE: PRT
<213> ORGANISM: Artificial Sequence
<220> FEATURE:
<223> OTHER INFORMATION: Description of Artificial Sequence: artificial
      protein (translation of SEQ ID No: 2)

<400> SEQUENCE: 1

Met Ala Ser Arg Arg Leu Leu Ala Ser Leu Leu Arg Gln Ser Ala Gln
 1               5                  10                  15

Arg Gly Gly Gly Leu Ile Ser Arg Ser Leu Gly Asn Ser Ile Pro Lys
                20                  25                  30

Ser Ala Ser Arg Ala Ser Ser Arg Ala Ser Pro Lys Gly Phe Leu Leu
            35                  40                  45

Asn Arg Ala Val Gln Tyr Ala Thr Ser Ala Ala Ala Pro Ala Ser Gln
        50                  55                  60

Pro Ser Thr Pro Pro Lys Ser Gly Ser Glu Pro Ser Gly Lys Ile Thr
 65                  70                  75                  80

Asp Glu Phe Thr Gly Ala Gly Ser Ile Gly Ala Met Asp Lys Ser Leu
                85                  90                  95

Ile Ile Phe Gly Ile Val Asn Ile Thr Ser Asp Ser Phe Ser Asp Gly
               100                 105                 110

Gly Arg Tyr Leu Ala Pro Asp Ala Ala Ile Ala Gln Ala Arg Lys Leu
           115                 120                 125

Met Ala Glu Gly Ala Asp Val Ile Asp Leu Gly Pro Ala Ser Ser Asn
       130                 135                 140

Pro Asp Ala Ala Pro Val Ser Ser Asp Thr Glu Ile Ala Arg Ile Ala
145                 150                 155                 160

Pro Val Leu Asp Ala Leu Lys Ala Asp Gly Ile Pro Val Ser Leu Asp
               165                 170                 175

Ser Tyr Gln Pro Ala Thr Gln Ala Tyr Ala Leu Ser Arg Gly Val Ala
           180                 185                 190

Tyr Leu Asn Asp Ile Arg Gly Phe Pro Asp Ala Ala Phe Tyr Pro Gln
       195                 200                 205

Leu Ala Lys Ser Ser Ala Lys Leu Val Val Met His Ser Val Gln Asp
   210                 215                 220

Gly Gln Ala Asp Arg Arg Glu Ala Pro Ala Gly Asp Ile Met Asp His
```

```
                  225                 230                 235                 240
           Ile Ala Ala Phe Phe Asp Ala Arg Ile Ala Ala Leu Thr Gly Ala Gly
                           245                 250                 255

Ile Lys Arg Asn Arg Leu Val Leu Asp Pro Gly Met Gly Phe Phe Leu
                       260                 265                 270

Gly Ala Ala Pro Glu Thr Ser Leu Ser Val Leu Ala Arg Phe Asp Glu
                       275                 280                 285

Leu Arg Leu Arg Phe Asp Leu Pro Val Leu Leu Ser Val Ser Arg Lys
                   290                 295                 300

Ser Phe Leu Arg Ala Leu Thr Gly Arg Gly Pro Gly Asp Val Gly Ala
           305                 310                 315                 320

Ala Thr Leu Ala Ala Glu Leu Ala Ala Ala Gly Gly Ala Asp Phe
                           325                 330                 335

Ile Arg Thr His Glu Pro Arg Pro Leu Arg Asp Gly Leu Ala Val Leu
                           340                 345                 350

Ala Ala Leu Lys Glu Thr Ala Arg Ile Arg
                       355                 360

<210> SEQ ID NO 2
<211> LENGTH: 1115
<212> TYPE: DNA
<213> ORGANISM: Artificial Sequence
<220> FEATURE:
<223> OTHER INFORMATION: Description of Artificial Sequence: artificial
      cDNA (gene fusion)

<400> SEQUENCE: 2
aattacattt acaattatcg atggcttctc ggaggcttct cgcctctctc ctccgtcaat     60
cggctcaacg tggcggcggt ctaatttccc gatcgttagg aaactccatc cctaaatccg    120
cttcacgcgc ctcttcacgc gcatccccta agggattcct cttaaaccgc gccgtacagt    180
acgctacctc cgcagcggca ccggcatctc agccatcaac accaccaaag tccggcagtg    240
aaccgtccgg aaaaattacc gatgagttca ccggcgctgg ttcgatcggt gccatggata    300
aatcgctcat cattttcggc atcgtcaaca taacctcgga cagtttctcc gatggaggcc    360
ggtatctggc gccagacgca gccattgcgc aggcgcgtaa gctgatggcc gaggggggcag    420 atgtgatcga cctcggtccg gcatccagca atcccgacgc cgcgcctgtt tcgtccgaca    480
cagaaatcgc gcgtatcgcg ccggtgctgg acgcgctcaa ggcagatggc attcccgtct    540
cgctcgacag ttatcaaccc gcgacgcaag cctatgcctt gtcgcgtggt gtggcctatc    600
tcaatgatat tcgcggtttt ccagacgctg cgttctatcc gcaattggcg aaatcatctg    660
ccaaactcgt cgttatgcat tcggtgcaag acgggcaggc agatcggcgc gaggcacccg    720
ctggcgacat catggatcac attgcggcgt tctttgacgc gcgcatcgcg gcgctgacgg    780
gtgccggtat caaacgcaac cgccttgtcc ttgatcccgg catgggtttt tttctggggg    840
ctgctcccga aacctcgctc tcggtgctgg cgcggttcga tgaattgcgg ctgcgcttcg    900
atttgccggt gcttctgtct gtttcgcgca atccttttct cgcgcgcgctc acaggccgtg    960 gtccggggga tgtcggggcc gcgacactcg ctgcagagct tgccgccgcc gcaggtggag   1020
ctgacttcat ccgcacacac gagccgcgcc ccttgcgcga cgggctggcg gtattggcgg   1080
cgctgaaaga aaccgcaagg attcgttaat ctaga                              1115

<210> SEQ ID NO 3
<211> LENGTH: 84
<212> TYPE: DNA
```

```
<213> ORGANISM: Artificial Sequence
<220> FEATURE:
<223> OTHER INFORMATION: Description of Artificial Sequence:
      oligonucleotide primer

<400> SEQUENCE: 3
ccatcgatgg cttctcggag gcttctcgcc tctctcctcc gtcaatcggc tcaacgtggc    60
ggcggtctaa tttcccgatc gtta                                           84

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ggaaactcca tccctaaatc cgcttcacgc gcctcttcac gcgcatcccc taagggattc    60
ctcttaaacc gcgccgtaca gtacgctacc tccgcagcgg                         100

<210> SEQ ID NO 5
<211> LENGTH: 93
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
caccggcatc tcagccatca acaccaccaa agtccggcag tgaaccgtcc ggaaaaatta    60
ccgatgagtt caccggcgct ggttcgatcg gtc                                 93

<210> SEQ ID NO 6
<211> LENGTH: 92
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
catgccatgg accgatcgaa ccagcgccgg tgaactcatc ggtaattttt ccggacggtt    60
cactgccgga ctttggtggt gttgatggct ga                                  92

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 7
gatgccggtg ccgctgcgga ggtagcgtac tgtacggcgc ggtttaagag gaatccctta    60
ggggatgcgc gtgaagaggc gcgtgaagcg gatttaggga                         100

<210> SEQ ID NO 8
<211> LENGTH: 94
<212> TYPE: DNA
<213> ORGANISM: Artificial Sequence
<220> FEATURE:
<223> OTHER INFORMATION: Description of Artificial Sequence:
      oligonucleotide primer
```

```
<400> SEQUENCE: 8
tggagtttcc taacgatcgg gaaattagac cgccgccacg ttgagccgat tgacggagga      60
gagaggcgag aagcctccga gaagccatcg atgg                                 94

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
aagcccccat ggataaatcg ctcatcattt tc                                   32

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
gctctagatt aacgaatcct tgcggtttct ttcagcg                              37
```